(12) United States Patent
Kim (10) Patent No.: US 7,524,518 B2
(45) Date of Patent: Apr. 28, 2009

(54) COMPOSITION FOR PROMOTING REGENERATION OF HARD TISSUES COMPRISING AN EXTRACT OF CORTEX EUCOMMIAE

(76) Inventor: Sung-Jin Kim, Chungryangn-Dong 60, Hanshin APT 104-2003, Oongdaamoon-Ku, Seoul (KR) 130-010

(*) Notice: Subject to any disclaimer, the term of this patent is extended or adjusted under 35 U.S.C. 154(b) by 242 days.

(21) Appl. No.: 11/074,138

(22) Filed: Mar. 7, 2005

(65) Prior Publication Data
US 2005/0158415 A1 Jul. 21, 2005

(51) Int. Cl.
*A01N 65/0017* (2006.01)
(52) U.S. Cl. ............................................ 424/725
(58) Field of Classification Search ............... None
See application file for complete search history.

(56) References Cited

U.S. PATENT DOCUMENTS

| | | | |
|---|---|---|---|
| 5,279,949 A * | 1/1994 | Nair | 435/123 |
| 6,280,751 B1 * | 8/2001 | Fletcher et al. | 424/401 |
| 6,280,776 B1 * | 8/2001 | Sha et al. | 424/728 |
| 6,419,930 B2 * | 7/2002 | Sato et al. | 424/195.11 |
| 6,905,714 B2 * | 6/2005 | Ong et al. | 424/769 |
| 2001/0046524 A1 | 11/2001 | Ong et al. | |
| 2002/0031559 A1 * | 3/2002 | Liang et al. | 424/725 |

FOREIGN PATENT DOCUMENTS

| | | |
|---|---|---|
| CN | 1200281 A | 12/1998 |
| JP | 402258725 A | 10/1990 |
| JP | 402258725 A * | 10/1990 |
| JP | 409249578 A | 9/1997 |

OTHER PUBLICATIONS

Metori et al., Biol. Pharm. Bull, 20 (3), 237-242, 1997.*
Metori et al., Biol Pharm. Bull. , 17 (7), 917-920, 1994.*
Li et al., Biol. Pharm. Bull., 21912), 1306-1310, 1998.*
Furutsu et al., Jpn. J. Toxicol. Environ. Health, 43 (2), 92-100, 1997.*
Acupuncture Today, 5 pages, "Cortex Eucommiae Ulmoidis (Du Zhong) and Latex Allergy", 2007.*
Medboo TCM Training, Traditional, "Common Herbs", Eucommia Bark (Du Zhong, Cortex Eucommiae), 2007, 2 pages.*
Herbasin, Herbisin Chinese herb database-Cortex Eucommiae (Du Zhong), 2007, 2 pages.*

* cited by examiner

*Primary Examiner*—Michael V Meller
(74) *Attorney, Agent, or Firm*—Stetina Brunda Garred & Brucker (57) ABSTRACT

The present invention discloses a composition for promoting regeneration of hard tissues comprising an extract of Cortex Eucommiae. It can be applied to prevent and treat hard tissue disorders such as osteoporosis and periodontal disease followed by alveolar bone destruction. It can also be used to stimulate growth of children.

7 Claims, 9 Drawing Sheets

COMPOSITION FOR PROMOTING REGENERATION OF HARD TISSUES COMPRISING AN EXTRACT OF CORTEX EUCOMMIAE

BACKGROUND OF THE INVENTION

Hard tissues in humans are largely classified as bones and teeth. The representative diseases caused by hard tissue disorders are osteoporosis and periodontal diseases. Bones are essential for locomotion and play an important role in calcium metabolism. With age, incidences of bone fracture, osteoporosis, and severe periodontal disease accompanied by alveolar bone destruction increase significantly.

Teeth, as major components of the digestive system, are essential for mastication. Maintaining teeth in good condition is essential for satisfaction in eating and enjoying the taste of food, thereby especially increasing the quality of life for the elderly. Thus, the prevention and treatment of these aging-related diseases draw tremendous attention from societies with high percentages of elderly people.

Hard tissues undergo constant remodeling through bone formation (via osteoblast) and bone resorption (via osteoclast) and maintain homeostasis. Such metabolism is regulated by systemic hormones as well as local factors. When bone resorption rates surpass bone formation rates by a variety of factors and bone mass decreases below a critical level, bone-related diseases such as osteoporosis and periodontal disease occur.

As a biochemical index of osteoblast activity, alkaline phosphatase, Type 1 collagen, and osteocalcin are used clinically. Alkaline phosphatase is a initial index of osteoblast activity and starts to decrease as mineralization of matrix begins. Collagen is a bone matrix protein and represents approximately 90% of bone organic molecules (Schonau and Rauch, Horm. Res., 49 (suppl 5): 50-59, 1997). The majority of collagens is type 1 collagen made from a same gene present in the skin and type 5 collagen is present in a small quantity.

Collagen has a number of other functions other than as a structural protein. More specifically, it may (1) provide a place for mineral to precipitate, (2) be involved in the growth and differentiation of osteoblast, and/or (3) play an important role in mineralization and bone remodeling. Hydroxyproline represents approximately 14% of collagen contents and this formulation is relatively constant. Moreover, osteocalcin is a calcium binding protein which is expressed during the mineralization of matrix and is typically used as an index of osteoblast activity in its later stages.

In the osteoblast cells, ERK2 (Extracellular signal-regulated kinase 2) is induced by bone-active agents such as PDGF-BB, EGF, Insulin, IGF-1, Phorbol ester, and Estrogen. ERK is known to play an important role in the growth of osteoblast cells (Hipskind, B. A., Bilbe, G., Frontiers in Bioscience, 3, d804-816, 1998).

Cortex Eucommiae is the dried stem bark of Eucommia ulmoides Oliv. Its known components are mainly lignans and iridoids. In addition, erythro-/threoguaiacylglycerol, ulmoprenol, nonacosane, $\beta$-sitosterol, betulin, betulinic acid, ursolic acid and vanillic acid are also present as its components. It is known to have a variety of actions such as hypotensive, anti-hyperlipidemic, sedative and analgesic, anti-inflammatory, reticular phagocytic and diuretic effects (Chinese Materia Medica 1998). Extracts of Cortex Eucommiae are known to be very safe since their oral administrations of 15-25 g/kg to mouses did not cause death. However, their actions in the bone cells are not yet determined.

BRIEF SUMMARY OF THE INVENTION

While I have been studying for many years to develop a new drug originating from natural products, it was found that extracts of Cortex Eucommiae have significant effects on the osteoblast cells such as growth promoting action and stimulation of collagen synthesis and alkaline phosphatase activity. Thus, these properties could be utilized for the development of a hard tissue regenerating agent.

In this respect, the present invention is related to a Cortex Eucommiae extract. The composition of the present invention contains components extracted from Cortex Eucommmiae with low class alcohols or organic solvents and has the following actions: (1) Inducing the differentiation and mineralization of osteoblasts via activation of alkaline phosphatase; (2) Strengthening bone matrix by increasing collagen synthesis; (3) Inducing growth and differentiation of osteoblasts by stimulating ERK2 (Extracellular signal-Regulated Kinase 2). These properties of the Cortex Eucommiae extract are useful in the prevention and treatment of osteoporosis, and hard tissue disorders such as alveolar bone destruction or metabolic bone diseases including periodontal diseases.

BRIEF DESCRIPTION OF THE DRAWINGS

These as well as other features of the present invention will become more apparent upon reference to the drawings wherein.

DETAILED DESCRIPTION OF THE INVENTION

This invention is related to a composition for promoting hard tissue regeneration comprising a Cortex Eucommiae extract. The cortex Eucommiae extract can be obtained by extraction with water, low alcohol or organic solvents. The low alcohol may be methanol, ethanol, etc., and the organic solvents may be acetone, chloroform, methylene chloride, ether, ethylacetate, hexane, etc. In detail, the Cortex Eucommiae extract in the present invention can be obtained according to the following procedure: Cortex Eucommiae was mixed with about 5 to 50-fold (preferably 10-fold) extraction solution and was incubated at 5° C. to 80° C. (preferably 30° C. to 55° C.) for 15 min to 48 hrs (preferably 30 min to 12 hrs). The resulting extract was subjected to filtration, concentration and freeze dry.

The Cortex Eucommiae extract in the composition of the present invention activates alkaline phosphatase activities in the osteoblast cells, thereby inducing differentiation and mineralization of the cells. It also stimulates collagen synthesis, thereby strengthening the matrix of hard tissues. In addition, the Cortex Eucommiae extract has the ability to activate ERK2 (Extracellular signal-Regulated Kinase 2), which may play an important role in the induction of growth and differentiation of osteoblast cells. Thus, the composition containing a Cortex Eucommiae extract in the present invention could be used as a pharmaceutical agent to promote regeneration of hard tissues. It is useful in the prevention and treatment of hard tissue disorders such as osteoporosis and periodontal disease accompanied by alveolar bone destruction.

Furthermore, since the Cortex Eucommiae extract lacks cytotoxicity, it is safe and therefore could be widely applied regardless of the gender, age and health status. Additionally, it can be added to a currently available pharmaceutical agent used for bone diseases to bring about synergistic effects. It can also be used to stimulate growth of children.

The composition of the present invention can comprise a Cortex Eucommiae extract by itself. However, the composition can contain pharmaceutical additives such as antioxidants, flavors and perfumes, stiffening agent, sweetening agents, tablet binders, vehicles, tablet and/or capsule diluents, etc. In addition, it can be mixed with other bio-active molecules to thereby increase a desired effect. For example, if the Cortex Eucommiae extract is combined with an anti-inflammatory agent, it can produce outstanding effects against periodontal disease. The composition for promoting hard tissue regeneration in the present invention can be administered in clinical situations as pharmaceutical preparations in the form of solid, semi-solid or liquid suitable for oral or perenteral administration by combining pharmaceutically allowed additives and the Cortex Eucommiae extract. The pharmaceutically allowed additives used for this purpose could be solid or liquid and one or more of the diluent, flavors and perfume, emulsifying and/or solubilizing agent, tablet and/or capsule lubricant, sweetening agent and tablet disintegrant.

Examples of preparation made from the composition of the present invention are tablets, pills, powders, granules, spirits, infusions, decoctions, tinctures, elixirs, suspensions, drinks, emulsions, solutions, syrups, sachet, aerosols, capsules, injections, sterilized powders, etc. The pharmaceutical composition of the present invention may be administered via oral, subcutaneous, intramuscular, intravenous, transdermal routes, etc.

In case of humans, administration dosage of the Cortex Eucommiae is 1 to 1,000 mg/kg body weight per day, preferably 10 to 100 mg/kg body weight per day. The dosage can be administered once or it can be divided and administered. However, the actual dose administered should be understood in terms of various related factors such as kind of disease to treat, administration route, age of patient, gender and weight, and the condition of disease, etc. Therefore, the above-mentioned dosage does not limit the range of the present invention by any ways. The followings are examples of preparation of the present invention, but the present invention is not limited to these examples.

EXAMPLE 1

Preparation of Cortex Eucommiae Extract

Cortex Eucommiae (300 g) was cut into small pieces and extracted three times with 70% methanol (1000 ml) for 3 hrs. The resulting methanol extract was filtered and concentrated with rotary evaporator and dried by freeze dryer.

EXAMPLE 2

Effects on the Alkaline Phosphatase Activities

Cell culture—UMR-106 cells (ATCC CRL-1661, Rockville, Md.) and MC3T3-E1 cells were grown in DMEM media with 10% fetal calf serum in 5% humidified $CO_2$ atmosphere at 37° C. in the presence of 100 IU/ml penicillin and 100 µg/ml streptomycin. The cells were incubated with serum deprived media containing 0.1% serum bovine albumin for 24 hrs before the addition of Cortex Eucommiae extract.

Measurement of Alkaline Phosphatase activity—The measurement of alkaline phosphatase activity was carried out as described earlier (Cortizo, A. M., Etcheverry, S. B. Mol. Cell Biochem. 145, 97-102, 1995). After incubation with Cortex Eucommiae extract (10 µg/ml) for 24 hrs, the cell layer was washed with PBS and solubilized with 0.1% Triton X-100. Following brief sonication and centrifugation at 5,000 rpm for 3 min, aliquots of the supernatant were used for measurement of alkaline phosphatase activity using a alkaline phosphatase kit (Youngdong Pharmaceutical Co., Korea).

Figure 1:
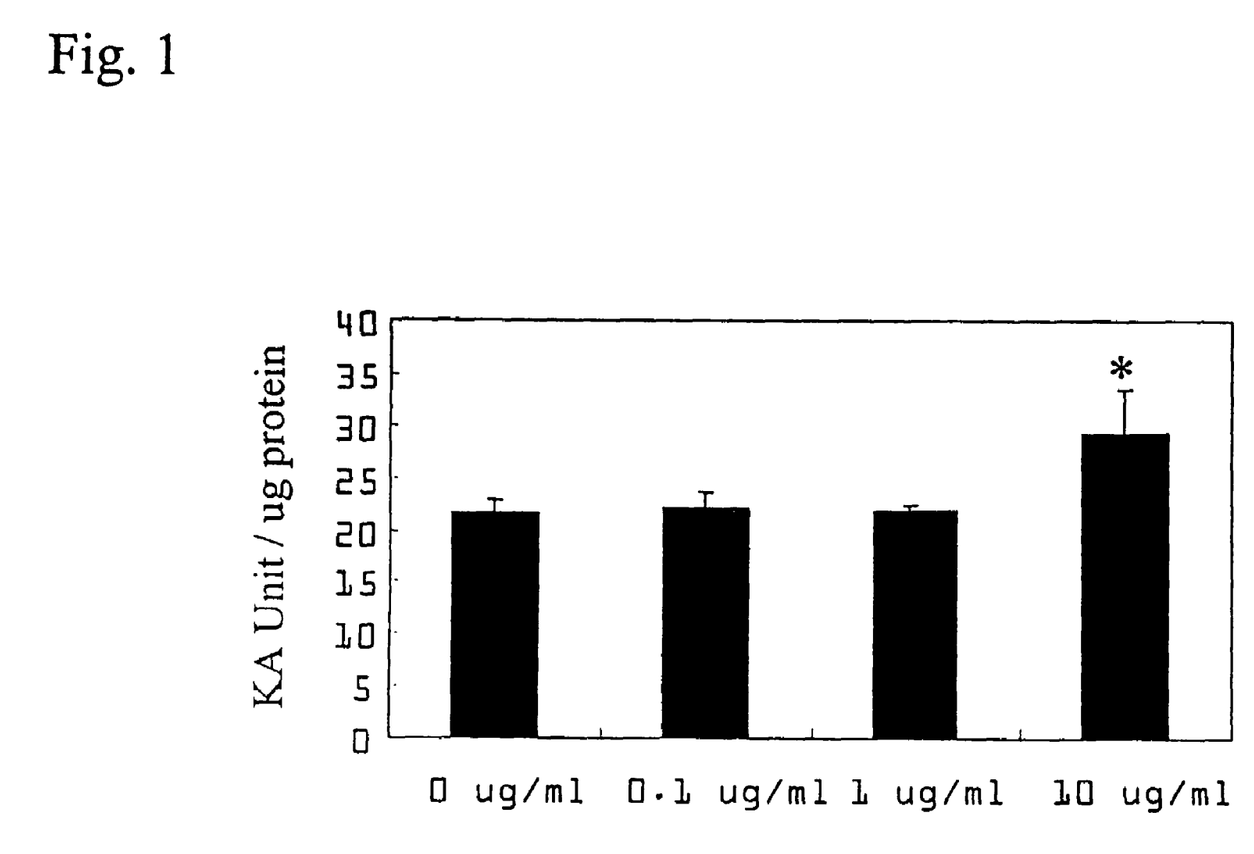
FIG. 1 represents the effect of the Cortex Eucommiae extract on the alkaline phosphatase activities in the osteoblast-like UMR-106 cells when the extract was added to the cell for 1 day. *=$p<0.05$ versus controls.
Figure 2:
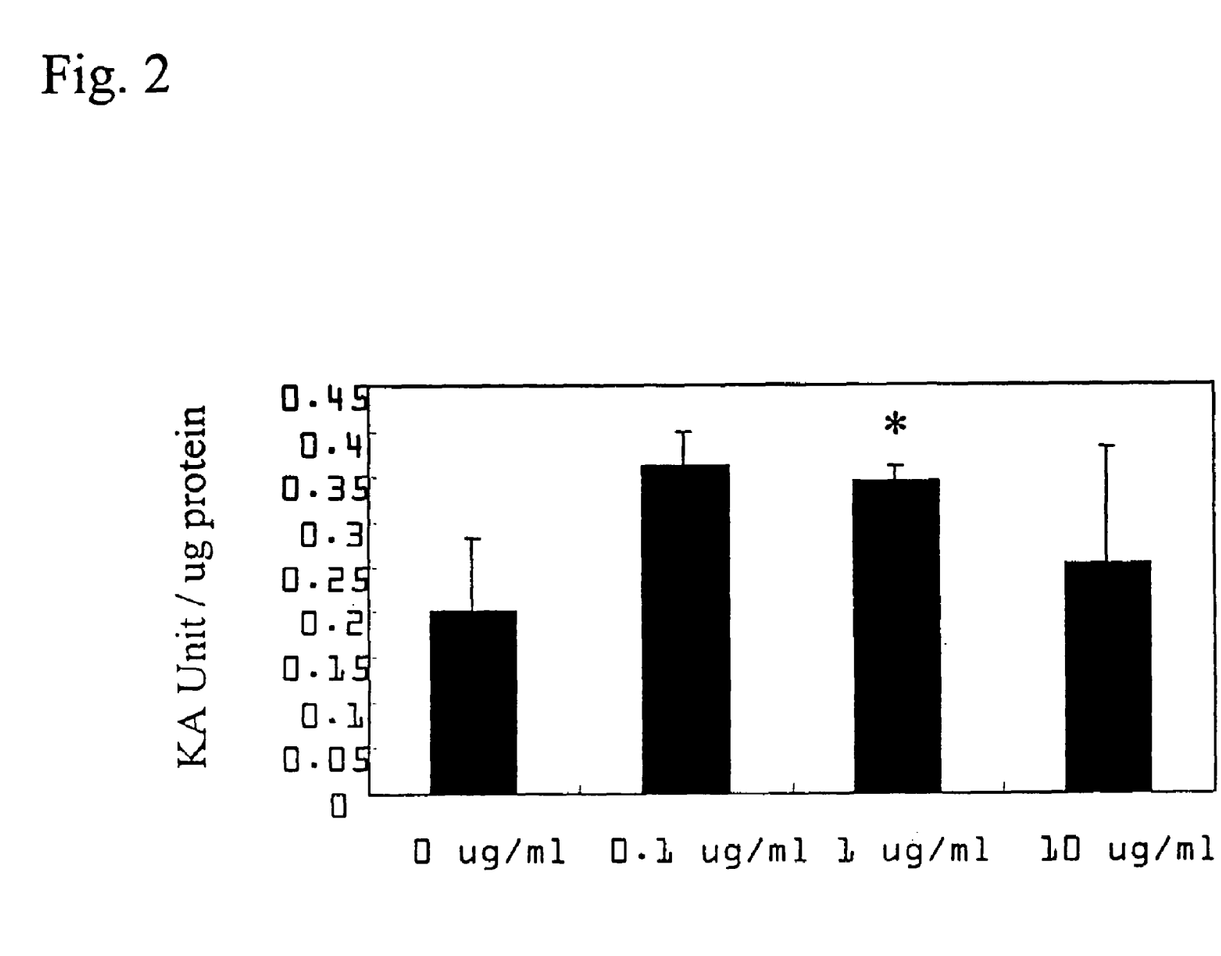
FIG. 2 represents the effect of the Cortex Eucommiae extract on the alkaline phosphatase activities in the osteoblast-like UMR-106 cells when the extract was added to the cell for 2 days. *=$p<0.05$ versus controls.
Figure 3:
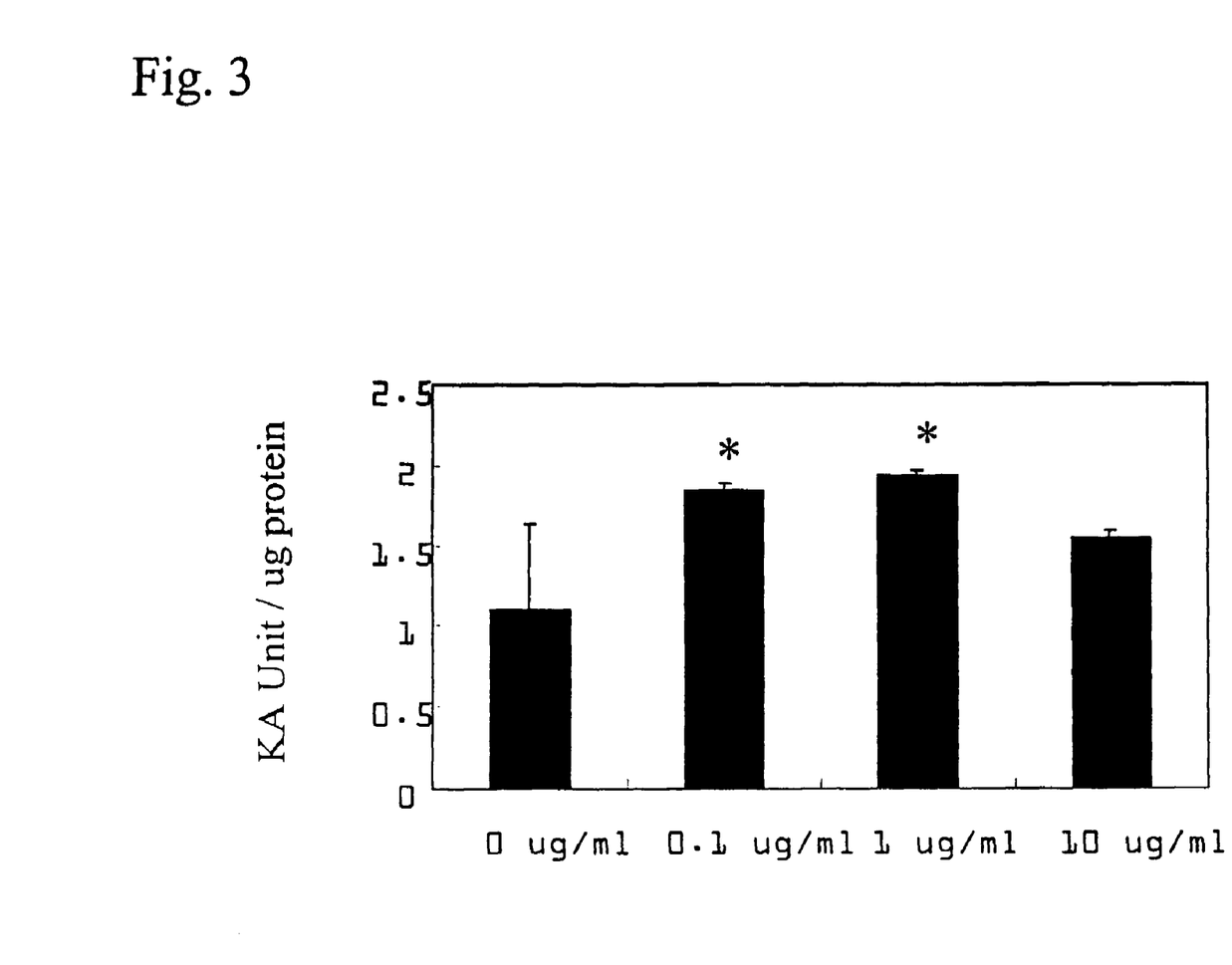
FIG. 3 represents the effect of the Cortex Eucommiae extract on the alkaline phosphatase activities in the osteoblast MC3T3-E1 cells when the extract was added to the cell for 7 days. *=$p<0.05$ versus controls.

Treatment of the Cortex Eucommiae extract at the concentration of 10 µg/ml for 1 day in UMR-106 cells stimulated alkaline phosphatase activity by 32% as compared to control (FIG. 1). When the MC3T3-E1 cells were incubated with Cortex Eucommiae extract at the concentrations of 0.1 µg/ml, 1 µg/ml and 10 µg/ml for 2 days, alkaline phosphatase activities were stimulated by 79%, 72% and 25% as compared to control, respectively (FIG. 2), whereas treatment of the cells with Cortex Eucommiae extract at the concentrations of 0.1 µg/ml, 1 µg/ml and 10 µg/ml for 7 days caused the increase of alkaline phosphatase activity by 67%, 74% and 39% as compared to control, respectively (FIG. 3). Thus, Cortex Eucommiae extracts may play an important role in the mineralization of bone cells by inducing differentiation of osteoblast cells via stimulation of alkaline phosphatase activity.

EXAMPLE 3

Effects on the Collagen Contents

Collagen contents were analyzed using the Sircol® collagen assay kit (Biocolor Ltd., Northern Ireland) as described earlier (Kim S J, Chun, J Y, Kim M S, Biochem. Biophys. Res. Commun. 278, 712-718, 2000).

Figure 4:
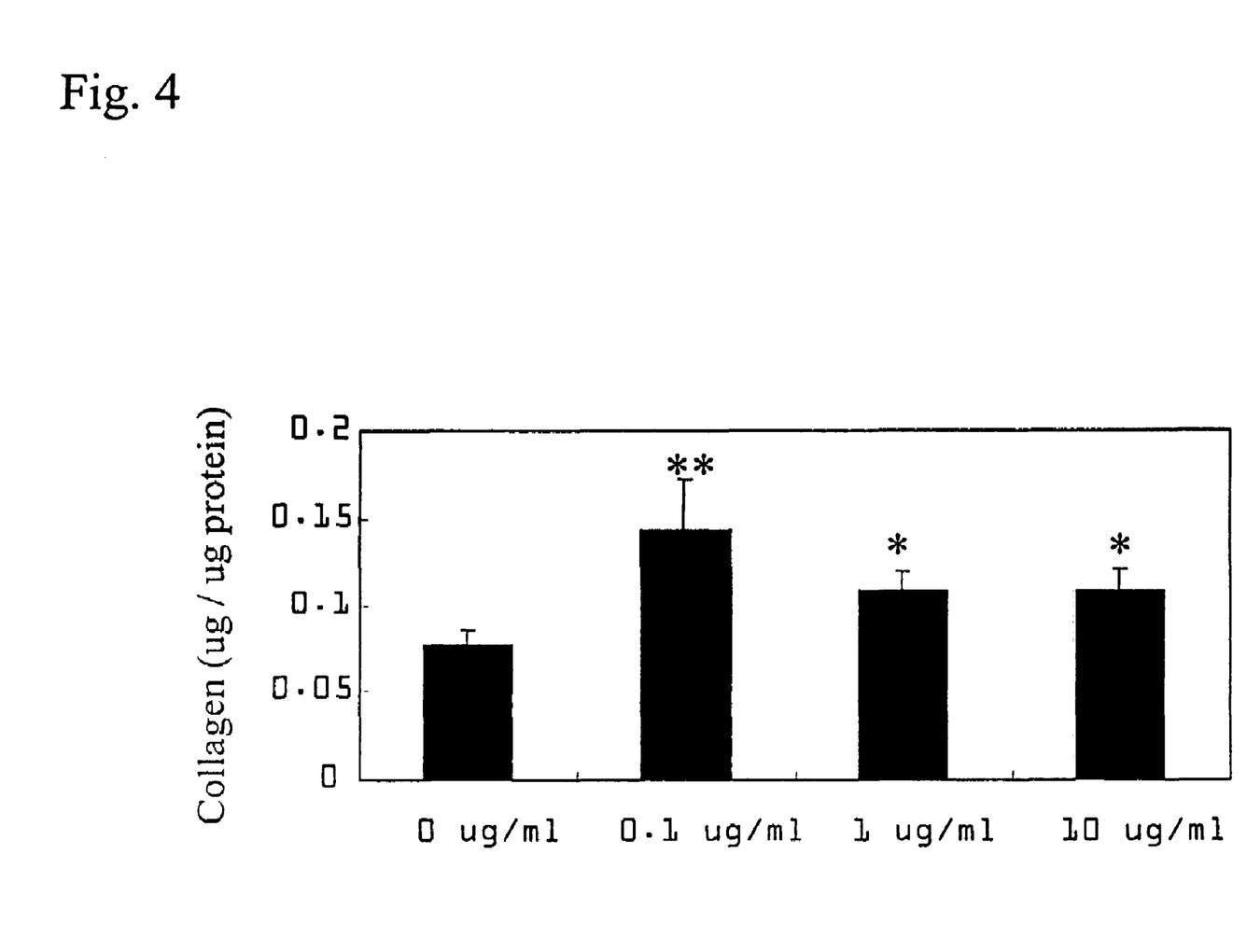
FIG. 4 represents the effect of the Cortex Eucommiae extract on the collagen synthesis in the osteoblast-like UMR-106 cells. *=$p<0.05$ versus controls; **=$p<0.01$ versus controls.
Figure 5:
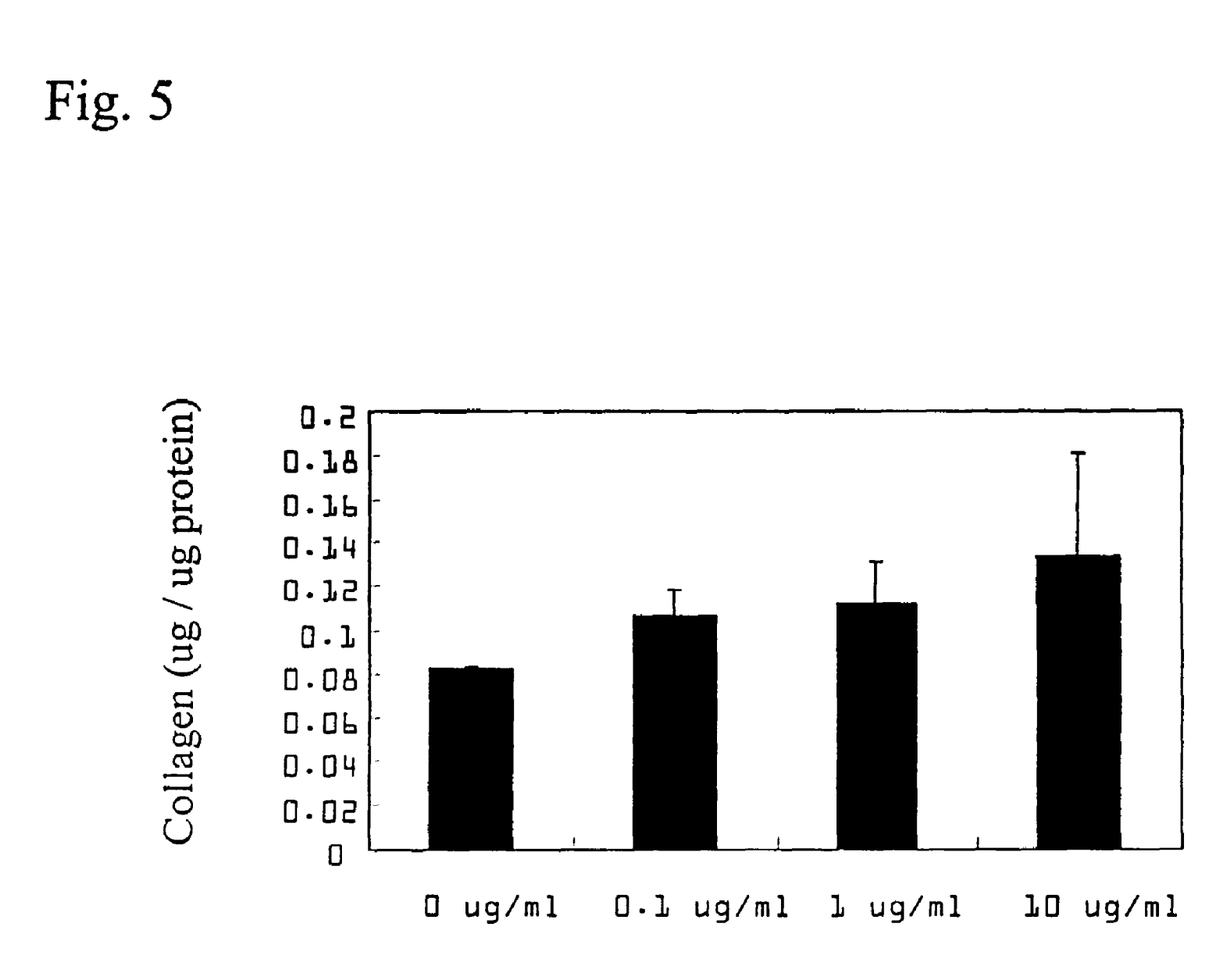
FIG. 5 represents the effect of the Cortex Eucommiae extract on the collagen synthesis in the osteoblast MC3T3-E1 cells.

When the UMR-106 cells were incubated with Cortex Eucommiae extract for 24 hrs at the concentrations of 0.1 µg/ml, 1 µg/ml and 10 µg/ml, the collagen synthesis was stimulated by 86%, 40% and 40% as compared to control, respectively (FIG. 4). Similarly, when the MC3T3-E1 cells were incubated with Cortex Eucommiae extract for 24 hrs at the concentrations of 0.1 µg/ml, 1 µg/ml and 10 µg/ml, the collagen synthesis was stimulated by 30%, 37% and 63% as compared to control, respectively (FIG. 4). Thus, it is obvious that the Cortex Eucommiae extract can strengthen the matrix of hard tissues by increasing collagen synthesis.

EXAMPLE 4

Effects on the ERK2 Activities

ERK2 (Extracellular signal Regulated Kinase 2) is an important signal transducing protein, which links the process of the activation of cell surface receptors in response to growth factors to cell growth, differentiation and gene expression (Siddhanti et al., Endocrinology, 136, 4834-4841 (1995); Hipskind and Bilbe, Front. Biosci., 1, D804-816, 1998). The UMR-106 cells were treated with Cortex Eucommiae extract at the concentration of 10 μg/ml for 0 min, 10 min or 30 min, and cell lysates were subjected to SDS-PAGE and followed by a Western blot analysis using ant-phospho ERK2 antibody (New England Biolab, USA).

Western blot analysis—Electrotransfer of proteins from the gels to nitrocelluose paper (Schleicher & Schuell) was carried out for 1 hr at 100 V (constant) as described by Towbin et al. [Towbin, H., Staehelin, J. and Gordon, J., Electrophoretic transfer of proteins from polyacrylamide gels to nitrocellulose sheets: procedure and some applications. *Proc. Natl. Acad. Sci. U.S.A.* 76: 4350-4354, 1979]. The filter papers were preincubated for 1 hr at 23° C. with PBS containing 0.1% Tween 20 and 3% bovine serum albumin and washed three times with PBS containing 0.1% Tween 20 for 10 min each. The blots were probed with primary antibodies (ERK2 or phospho-ERK2) for 1 hr at 23° C. The blots were then incubated with HRP-conjugated anti-rabbit IgG for 30 min and washed five times with PBS containing Tween 20 for 10 min each. The detection of immobilized specific antigens was carried out by ECL (NEN) (Harlow E. and Lane D., Antibodies: A laboratory manual., 726, 1988).

Figure 6:
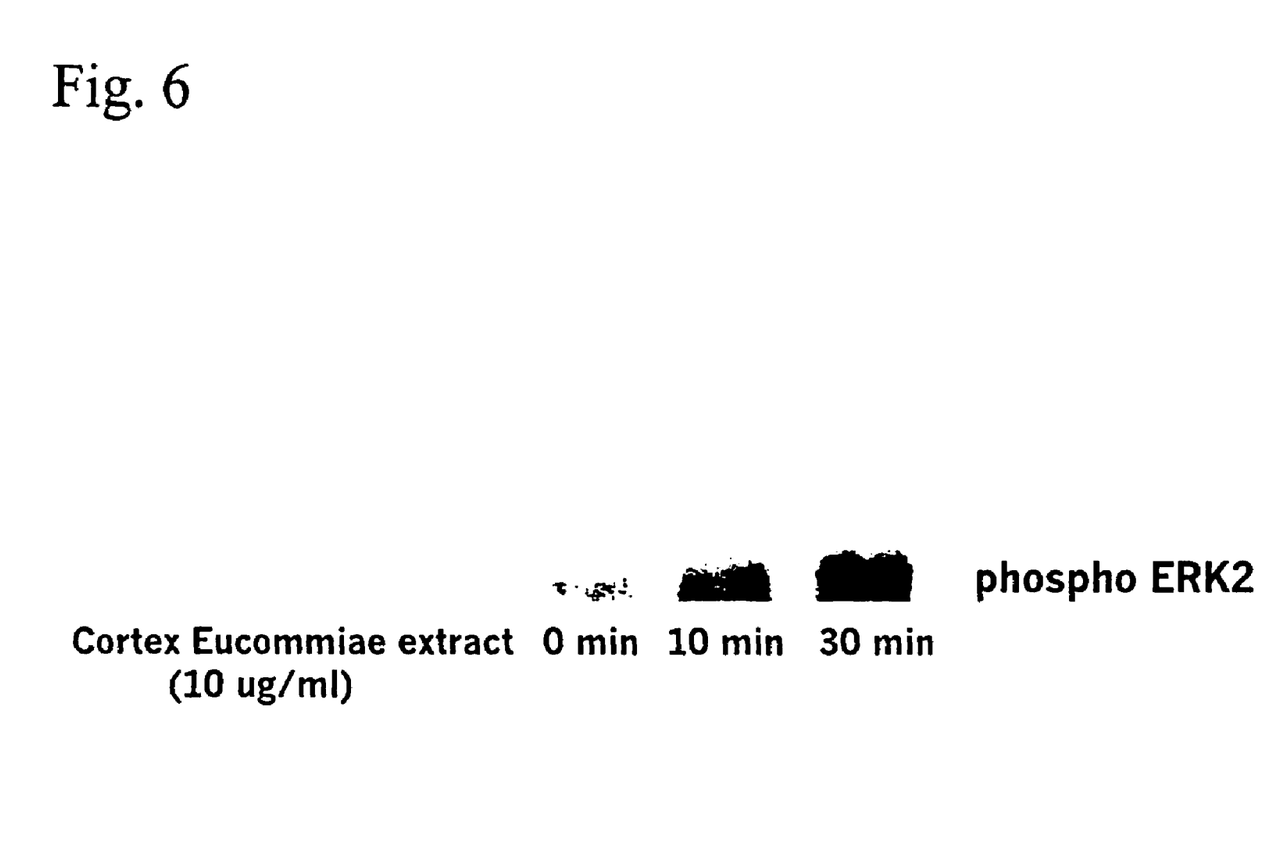
FIG. 6 represents the effect of the Cortex Eucommiae extract on the induction of ERK2 activities in the osteoblast-like UMR-106 cells.

It was found that Cortex Eucommiae extract has the ability to stimulate ERK2 activity in a time-dependent manner with a peak activity observed at 30 min as evidenced by the occurrence of phosphorylated ERK2 band (FIG. 6). These results indicate that the Cortex Eucommiae extract may induce cell growth and differentiation of osteoblast cells by stimulating ERK2 activity.

EXAMPLE 5

Cell Proliferation Assay

Culture of the MC3T3-E1 cells were carried out as described in the example 2 section.

Figure 7:
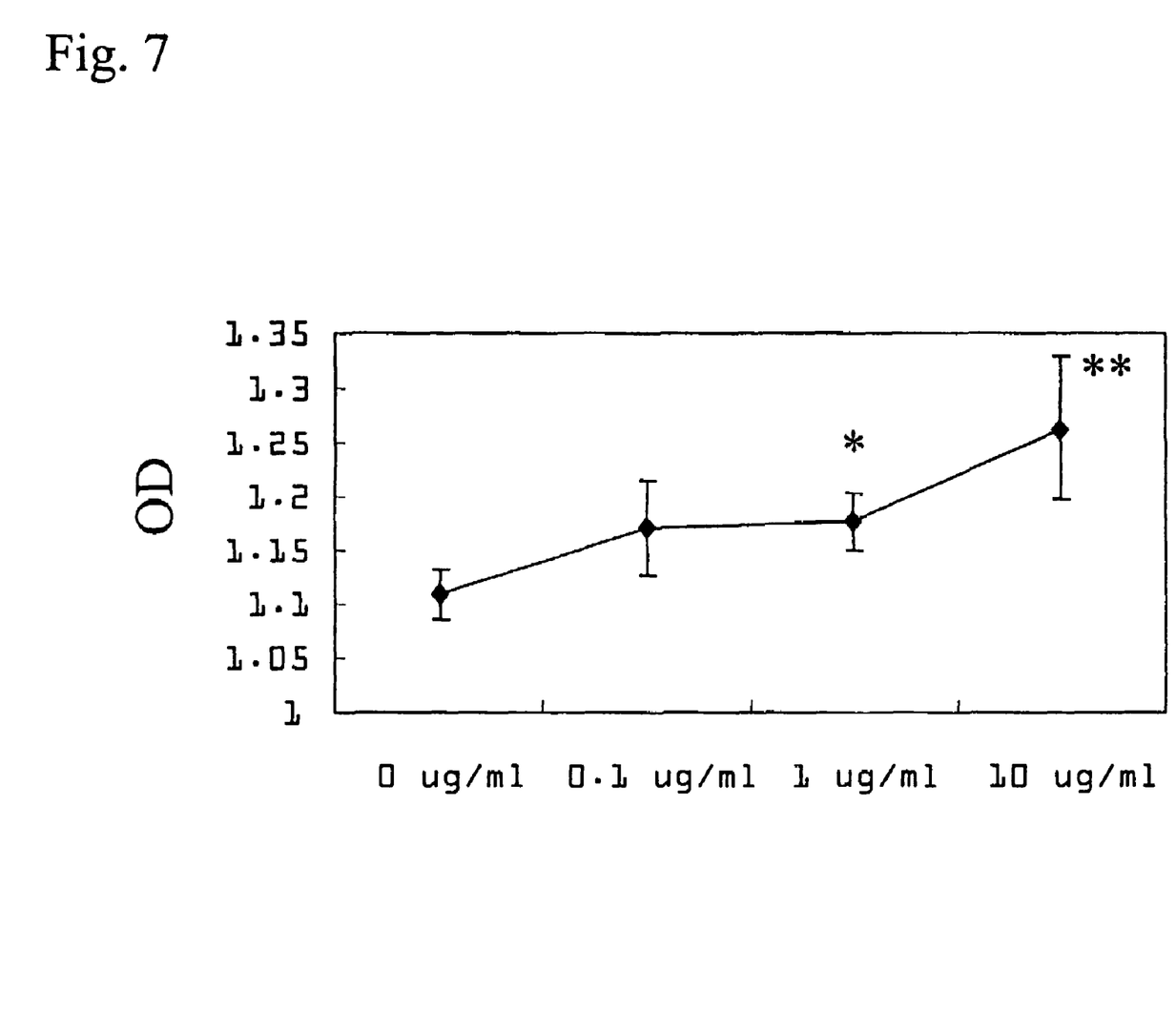
FIG. 7 represents the induction of cell growth by the Cortex Eucommiae extract in the osteoblast MC3T3-E1 cells. *=$p<0.05$ versus controls; **=$p<0.01$ versus controls.

A cell proliferation assay was carried out as described earlier (Etcheverry, S. B., Crans, D. C., Keramidas, A. D., and Cortizo, A. M., Archiv. Biochem. Biophys. 338, 7-14, 1997). Briefly, after incubation with Cortex Eucommiae extract (10 μg/ml) for 24 hrs, the cells in 24-well plates were washed with Phosphate Buffered Saline (PBS) and fixed with 5% glutaraldehyde/PBS at room temperature for 10 min. Then, they were stained with 0.5% crystal violet/25% methanol for 10 min. After that, the dye solution was discarded and the plate was washed with water and dried. The dye taken up by the cells was extracted using 0.5 ml/well 0.1M glycine/HCl buffer, pH3.0/30% methanol and transferred to test tubes. Absorbance was read at 540 nm. The Cortex Eucommiae extract caused an increase of the cell growth in a dose dependent manner (FIG. 7).

EXAMPLE 6

Cytotoxicity Tests (MTT Assay)

Culture of the UMR-106 cells and MC3T3-E1 cells were carried out as described in the example 2 section.

The cells were plated in 96 well plates at a density of $1 \times 10^5$ cells/well. Following Cortex Eucommiae extract treatment at the concentration of 0 μg/ml, 0.1 μg/ml, 1 μg/ml, 10 μg/ml, 100 μg/ml for 24 hrs, the cells were treated with MTT (0.5 mg/ml) and allowed to incubate for 3 hrs. The culture media were removed and the cells were subjected to lysis in the presence of 100 μl of DMSO and 10 μl of Sorenson glycine buffer and the absorbance was measured with spectrophotometer at 540 nm [Mosmann T., Rapid calorimetric assay for cellular growth and survival application to proliferation and cytotoxicity assay. *J Immunol, Method,* 65: 55-63, 1983].

Figure 8:
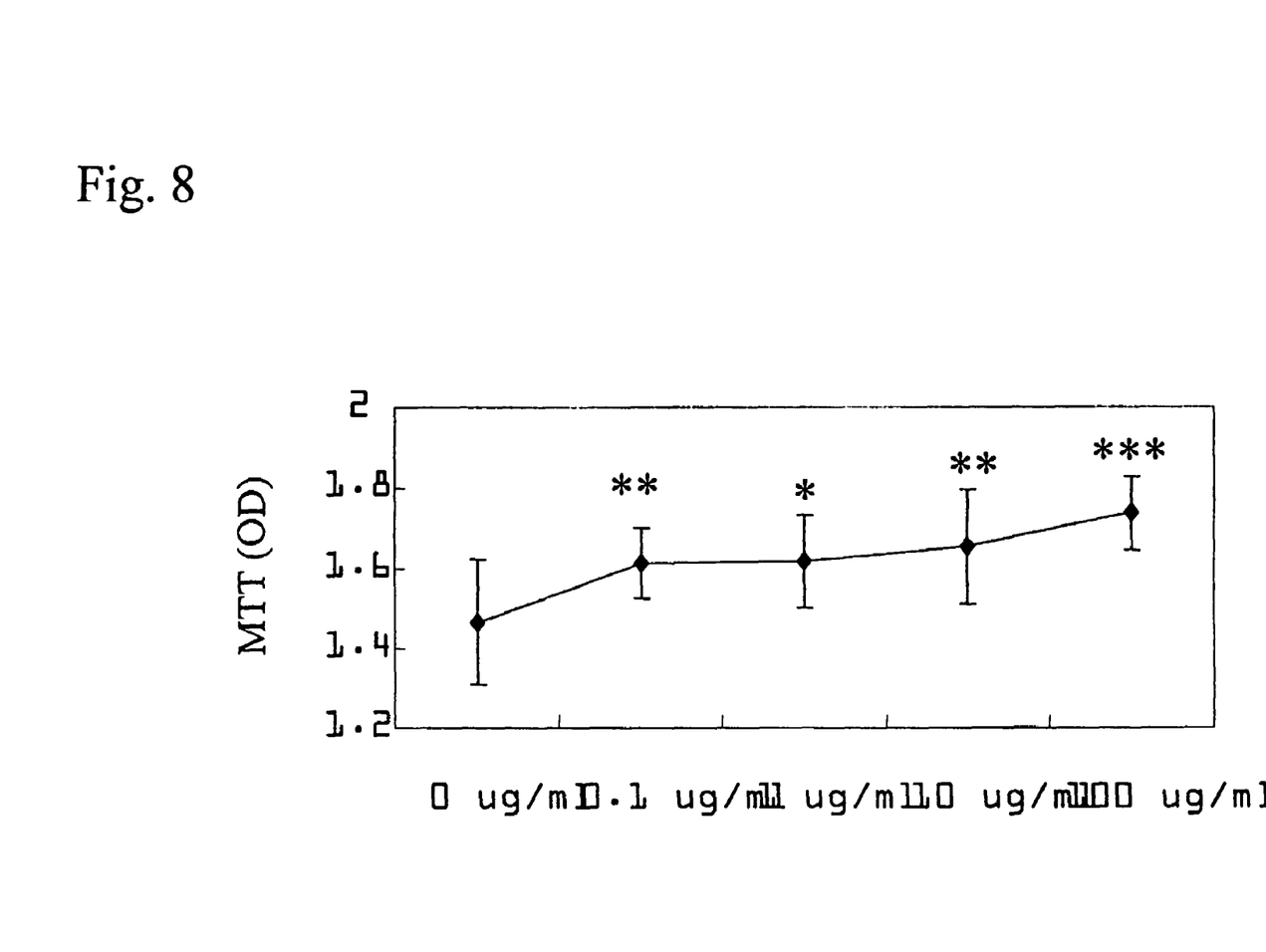
FIG. 8 represents the effect of the Cortex Eucommiae extract on cell viability in the osteoblast-like UMR-106 cells. *=$p<0.05$ versus controls; =$p<0.01$ versus controls; *=$p<0.001$ versus controls
Figure 9:
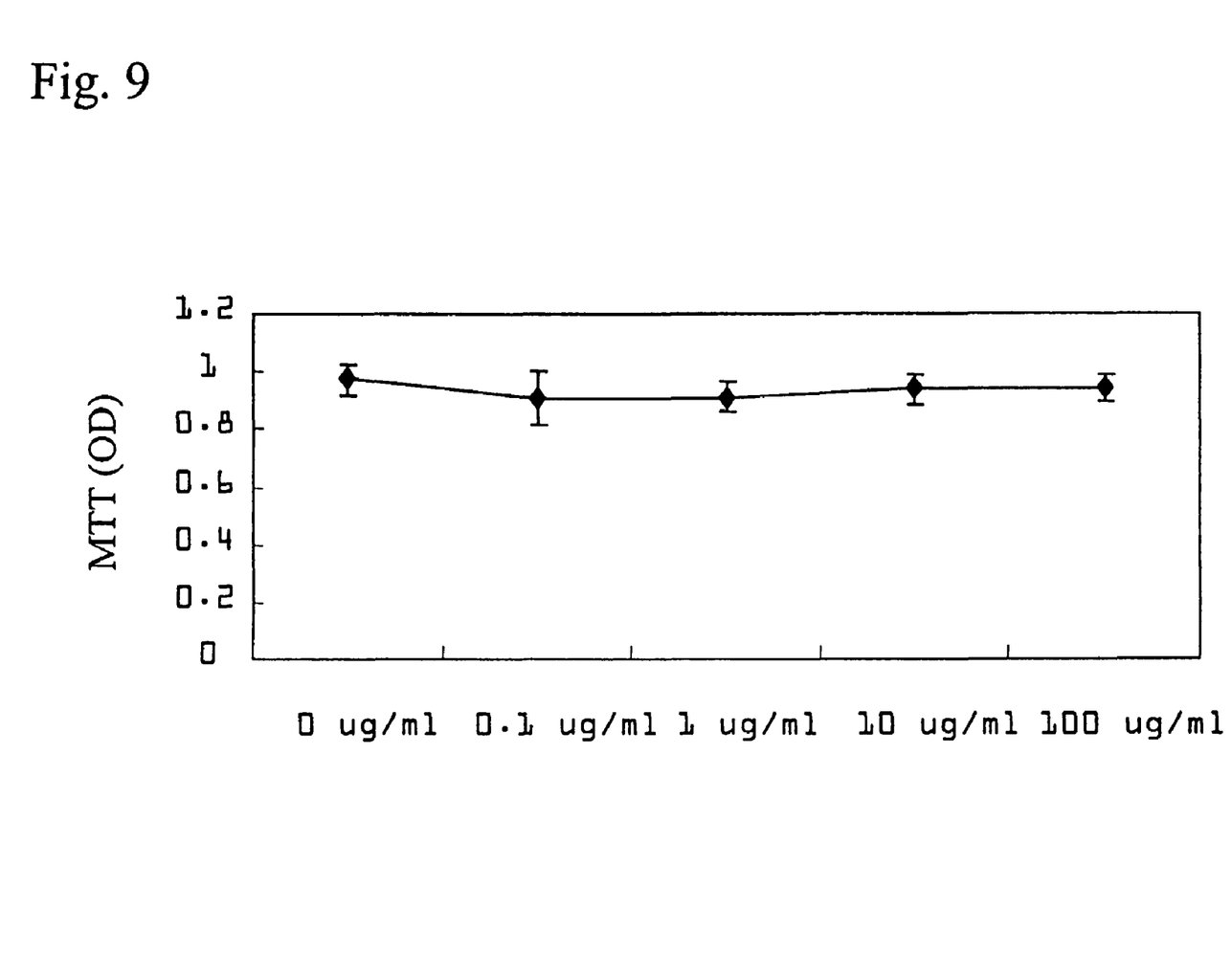
FIG. 9 represents the effect of the Cortex Eucommiae extract on cell viability in the osteoblast MC3T3-E1 cells.

Treatment of the UMR-106 and MC3T3-E1 cells with the Cortex Eucommiae extract did not cause any decrease in the cell viability at all concentrations tested (FIG. 8 and FIG. 9). Even at the 100 μg/ml which is 10 times higher than the effective concentration, there was no decrease in the cell viability. These results indicate that the Cortex Eucommiae extract is not cytotoxic. Strikingly, the Cortex Eucommiae extract rather induced an increase in the cell viability.

In conclusion, the composition of the present invention is a promoter of regenerating hard tissues which can be applied to prevent and treat hard tissue disorders such as osteoporosis, alveolar bone destruction etc. Since it is very safe, it could be widely used regardless of gender, age or status of health. It can be used to induce synergistic effects as it is added to other drugs used for bone diseases. In addition, it can be used to increase growth of children.

Statistics: All values were expressed as the mean±SEM. Comparison between control and treated groups was performed by Student's t test.

Additional modifications and improvements of the present invention may also be apparent to those of ordinary skill in the art. Thus, the particular combination of parts described and illustrated herein is intended to represent only certain embodiments of the present invention, and is not intended to serve as limitations of alternative devices within the spirit and scope of the invention.

What is claimed is:

1. A method for treating periodontal disease in a mammal in need thereof by inducing growth and differentiation of osteoblast cells in said mammal, the method comprising administering to said mammal an extract of Eucommiae ulmoides Oliver stem bark that is obtained by extraction of the bark with methanol, the extract being administered in an amount sufficient to stimulate ERK2 activity.

2. The method of claim 1 wherein said mammal comprises a human.

3. The method of claim 1 wherein said extract is administered in an amount from 10 to 100 mg per kg of body weight of said mammal.

4. The method of claim 1 wherein said extract is administered via an administration route selected from the group consisting of oral administration, subcutaneous injection, intramuscular injection, intravenous infusion and transdermal administration.

5. The method of claim 1 wherein said extract is administered on a daily basis.

6. The method of claim 1 wherein the mammal is suffering from periodontal disease accompanied by alveolar bone destruction.

7. The method of claim 1 wherein the wherein the extract is obtained by extraction of the bark with 70% methanol.

* * * * *